United States Patent [19]

Reynolds et al.

[11] Patent Number: 5,181,916
[45] Date of Patent: Jan. 26, 1993

[54] SURGICAL PROBE AND SMOKE ELIMINATOR

[75] Inventors: Valdon G. Reynolds, Bountiful; James L. Sorenson, Salt Lake City; Gordon S. Reynolds, Bountiful, all of Utah

[73] Assignee: Sorenson Laboratories, Inc., Salt Lake City, Utah

[21] Appl. No.: 693,229

[22] Filed: Apr. 26, 1991

[51] Int. Cl.$^5$ .......................................... A61B 17/36
[52] U.S. Cl. .................................. 606/16; 604/22; 604/313; 604/902
[58] Field of Search ................. 606/15, 16; 239/104, 239/110, 124, 290, 424.5; 15/322; 604/21, 22, 313, 315, 902

[56] References Cited

U.S. PATENT DOCUMENTS

| | | | |
|---|---|---|---|
| 1,540,805 | 6/1925 | Reichenbach | 239/290 |
| 2,243,285 | 5/1941 | Pope | 128/6 |
| 2,483,233 | 9/1949 | Price et al. | 128/244 |
| 3,710,798 | 1/1973 | Bredemeier | 128/303.1 |
| 3,732,858 | 5/1973 | Banko | 128/2 B |
| 3,736,938 | 6/1973 | Evvard et al. | 128/305 |
| 3,805,787 | 4/1974 | Banko | 128/276 |
| 3,812,855 | 5/1974 | Banko | 128/276 |
| 3,821,510 | 6/1974 | Muncheryan | 219/121 |
| 3,828,780 | 8/1974 | Morrison, Jr. | 128/275.1 |
| 3,865,113 | 2/1975 | Sharon et al. | 128/303.1 |
| 3,982,541 | 9/1976 | L'Esperance, Jr. | 128/303.1 |
| 4,266,549 | 5/1981 | Kimura | 128/303.1 |
| 4,600,420 | 7/1986 | Wydeven et al. | 55/501 |
| 4,619,672 | 10/1986 | Robertson | 55/316 |
| 4,638,800 | 1/1987 | Michel | 128/303 |
| 4,642,128 | 2/1987 | Solorzano | 55/217 |
| 4,735,603 | 4/1988 | Goodson et al. | 604/21 |
| 4,810,269 | 3/1989 | Stackhouse et al. | 55/267 |
| 4,826,513 | 5/1989 | Stackhouse et al. | 55/316 |
| 4,869,715 | 9/1989 | Sherburne | 604/22 |
| 4,901,716 | 2/1990 | Stackhouse et al. | 128/201.25 |
| 4,906,261 | 3/1990 | Mohajer | 55/256 |
| 4,921,492 | 5/1990 | Schultz et al. | 604/315 |
| 4,959,063 | 9/1990 | Kojima | 606/15 |
| 5,026,367 | 6/1991 | Leckron et al. | 604/21 X |

FOREIGN PATENT DOCUMENTS

| | | | |
|---|---|---|---|
| 402101 | 12/1990 | European Pat. Off. | 606/15 |
| 3415293 | 11/1985 | Fed. Rep. of Germany | 606/16 |
| 672883A5 | 1/1990 | Switzerland | |

OTHER PUBLICATIONS

Nezhat, Camran et al., "Smoke From Laser Surgery: Is There A Health Hazard", *Lasers in Surgery and Medicine*, vol. 7, pp. 376-382 (1987).

Smith, Jerome P., et al., "Evaluation of a Smoke Evacuator Used for Laser Surgery", *Lasers in Surgery and Medicine*, vol. 9, pp. 276-281 (1989).

*Primary Examiner*—David J. Isabella
*Assistant Examiner*—Mary Beth O. Jones
*Attorney, Agent, or Firm*—Workman, Nydegger and Jensen

[57] ABSTRACT

The invention comprises a handpiece for use in a surgical procedure which involves directing a surgical agent to a target area of a person's body which procedure produces an unwanted smoke plume. The handpiece includes both a probe for directing a surgical agent, such as a $CO_2$ laser beam, and a smoke eliminator for removing with suction the smoke created by the surgical procedure. The probe has no functional components for creating the laser beam, and is thus economical enough to be disposable after one use. The smoke eliminator includes a nozzle and/or an offset suction port so configured as to create a votrex flow in the smoke in the target area upstream in the fluid flow pathway of smoke through the hand piece from the distal tip of the hand piece.

21 Claims, 5 Drawing Sheets

SURGICAL PROBE AND SMOKE ELIMINATOR

BACKGROUND

1. Field of the Invention

The present invention is in the field of surgical devices which cut, burn, or cauterize tissue and which remove the smoke and vaporized particles created by the surgical devices. Specifically, the invention is primarily directed to an integral laser tip and smoke eliminator which efficiently removes harmful smoke and debris from the surgical site.

2. Background Art

Laser surgery has developed rapidly over the past several years. However, the procedure has been accompanied by at least one annoying problem, namely the production of a cloud of smoke and vaporized particles which tend to obscure the operation. Additionally, the smoke has a malodorous nature which tends to fill the room, causing objectionable reactions of all therein. Additionally, some studies have indicated that DNA from human papilloma virus may be included in the smoke. Thus, there is a health issue as well as an odor issue involved.

As a consequence, various smoke-plume elimination devices have been developed. A common feature is that all involve the use of a vacuum-suction device with a nozzle positioned near the laser impact area. Some such devices have required the use of two operators, one to hold and direct the handpiece involving the laser beam and the other to hold and direct the nozzle of the suction device. Some more sophisticated devices have combined the two into a single handpiece. Normally, such devices include optical components. Thus, the devices are too costly to throw away and must be sterilized for reuse.

BRIEF SUMMARY AND OBJECTS OF THE INVENTION

One of the principal objects of the present invention is to provide a handpiece adapted to cut, burn, or cauterize tissue by a surgical agent, which handpiece combines both a probe, such as for a laser beam, and a smoke eliminator into a single easily manipulatable handpiece which can be used by a single operator using only one hand. In this specification the term surgical agent is defined to include a laser beam, of whatever type, an electrocauterization scalpel, a freezing agent, a chemical agent, or other agent which will create harmful smoke or vaporized particles.

Another principal object of the invention is to provide a disposable handpiece which contains no optical or other laser functional components therein, and is otherwise configured so as to be so simple and inexpensive that it is economical to dispose of it after a single use.

Another principal object of the invention is to provide a method for removing smoke and associated vaporized particles emitted from the target area by establishing a vortex around the target area so as to improve the efficiency of the smoke eliminator.

Another principal object of the invention is to provide an apparatus which, in cooperation with a vacuum-suction means, creates a vortex at the tip of the smoke eliminator nozzle, thus significantly improving the efficacy of the device in removing smoke and associated vaporized particles.

The invention comprises both a method and apparatus for directing a surgical agent, such as a laser beam, to a target area, and for removing the smoke and associated vaporized particles created thereby.

The method comprises a procedure whereby a vacuum suction force is directed to the target area of a surgical agent by way of a transmitting conduit, which conduit may include an offset vacuum port and/or a plurality of nozzle orifices, so configured and emplaced as to result in a substantially circular swirling of suctioned fluid and particles, a vortex, around the target area.

The apparatus comprises a removable and disposable handpiece which includes a probe and a smoke eliminator. The probe comprises a first conduit for transmitting a surgical agent, such as, but not restricted to, a laser beam, from an articulating end of the laser device to the target area. The smoke eliminator comprises a second conduit through which are drawn the smoke and associated vaporized particles created at the target area utilizing a suction device coupled to the second conduit through an offset vacuum port. The movement of the smoke and vaporized particles in this manner defines a fluid flow pathway for the smoke and vaporized particles. A plurality of angularly directed nozzle orifices are positioned peripherally around the distal end of the second conduit. The nozzles orifices in cooperation with a vacuum-suction force, create a vortex in the smoke and vaporized particles upstream of the above-defined fluid flow pathway from the distal end of the second conduit. The first conduit and the second conduit are integral with each other or are affixed adjacent to each other. The first conduit is separable from the surgical agent device at a point distal of any optical or other functional elements utilized to generate or focus the surgical agent.

In one embodiment of the apparatus, the first conduit and the second conduit are configured as concentric tubes with the first conduit comprising the inner tube. The first conduit is open at both ends. The second conduit is closed at its proximal end and is open to outside space at its distal end, optionally by way of a plurality of specially configured nozzle orifices. Additionally, a suction port, comprising a third conduit, is affixed to the second conduit at or near the proximal end of the second conduit. The suction port communicates by way of an opening with the second conduit and by way of flexible tubing, with a vacuum-suction device.

The nozzle orifices are positioned around the periphery of the distal end of the second conduit and are configured and directed so as to effect a substantially circular flow of a fluid, thus creating a vortex. The axis of the suction port may be offset from the axis of the second conduit. When so offset it likewise creates a vortex. It has been found that a vortex is much more effective than the usual linear stream flow in collecting and removing the smoke and associated vaporized particles, probably due to the flow having a component directed inwardly, as in a cyclone.

The invention comprises further an optional and removable probe tip, configured so as to be removably attached to a peripheral segment of the distal end of the first conduit. This tip serves to approximately define the target area and to space the distal end of the probe at a predetermined distance from the target area, such as at the focal point of a laser beam. The removable probe tip is useful only in certain operations. The tip may be press-fit to the first conduit or may be threadably engaged therewith.

The handpiece is normally, but not necessarily, fashioned from a plastic material, and is cast in two pieces, the first conduit and the second conduit, which are subsequently cemented together at their proximal ends and in some embodiments at their distal ends.

Another embodiment of the invention utilizes a second conduit which is not concentric with the first conduit, but which is positioned adjacent the first conduit and affixed thereto. The distal end of the second conduit in some embodiments comprises a nozzle having a plurality of nozzle orifices, as before, closely associated with the distal end of the probe. The suction port in some embodiments may be offset. This embodiment may be more economical to manufacture.

As before noted, the handpiece is configured so as to be separable from the surgical agent device, such as a laser beam generator and focusing means, downstream from any optical or other functional elements utilized to generate or focus the surgical agent. Thus, the handpiece is very simple and can be manufactured at low cost. This results in the device being disposable in harmony with the trend in modern hospitals to utilize instruments, where feasible, which can be discarded rather than needing to be sterilized for reuse.

BRIEF DESCRIPTION OF THE DRAWINGS

Reference is next made to a brief description of the drawings, which are intended to illustrate different embodiments of the handpiece of the present invention with respect to the manner of making and using same in its presently understood best mode. The drawings and the detailed description which follow are intended to be merely illustrative and not otherwise limiting of the scope of the invention as set forth in the appended claims.

DETAILED DESCRIPTION OF THE PREFERRED EMBODIMENT

Figure 1:
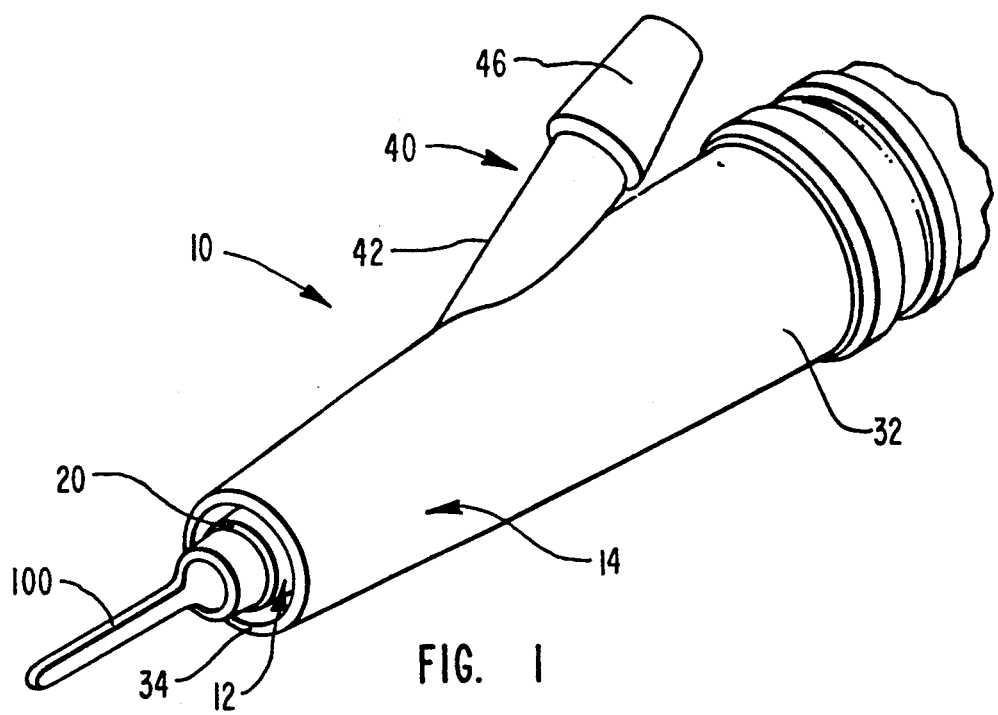
FIG. 1 is a perspective view of the handpiece showing a probe tip attached thereto and having an offset vacuum port.
Figure 2:
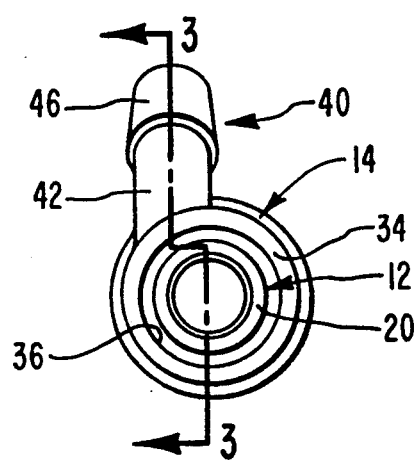
FIG. 2 is an end elevation view of the handpiece corresponding to FIG. 1 except the probe tip removed.
Figure 3:
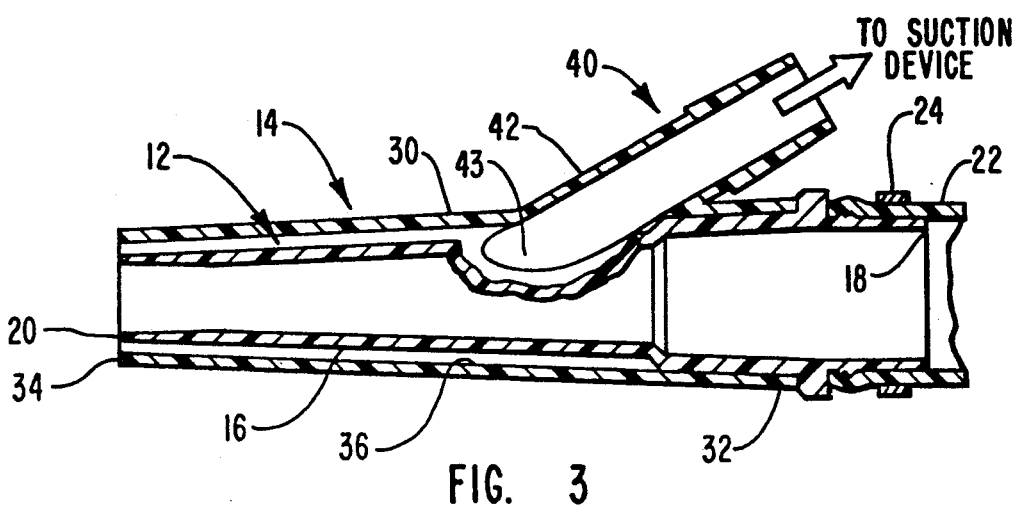
FIG. 3 is a cross-sectional view taken along line 3—3 of FIG. 2.

FIG. 1 depicts a perspective view of one embodiment of a handpiece 10 incorporating teachings of the present invention. Handpiece 10 comprises a probe 12 and a smoke eliminator 14, as shown best in FIGS. 3 and 4.

Probe 12 is fashioned as an elongate tubular member 16 having a proximal end 18 and a distal end 20. Proximal end 18 is preferably configured so as to have a larger outside diameter than the remainder of tubular member 16 so as to accommodate tubing 22 to be engaged therewith in a slip fit.

Tubing 22 connects the probe 12 to the surgical agent source, such as a $CO_2$ laser beam generator and associated optical components (not shown). Normally, this connection will incorporate articulating means such that the surgeon can manipulate the probe as needed. Additionally, the surgical agent may be other than a $CO_2$ laser beam. Neither the articulating means nor the surgical agent is likewise not a part of this invention. It is important to note, however, that the disconnect point of the probe 12 at proximal end 18 is downstream, or distal, from any optical elements or other functional components of the surgical agent source. Thus, probe 12 can be fashioned at a very low cost, and can be discarded after one use. The distal end 20 of probe 12 is open, as depicted, so as to allow passage of the laser beam or other surgical agent.

Smoke eliminator 14 comprises a tapered elongate tubular member 30 having a proximal end 32 and a distal end 34. As shown, tubular member 30 is concentric with tubular member 16, thus providing an annular space 36 therebetween. Proximal end 32 is fashioned so as to be attached to proximal end 18 of tubular member 16, such as by cementing, although this is but one of several ways for accommodating the attachment.

Figure 5:
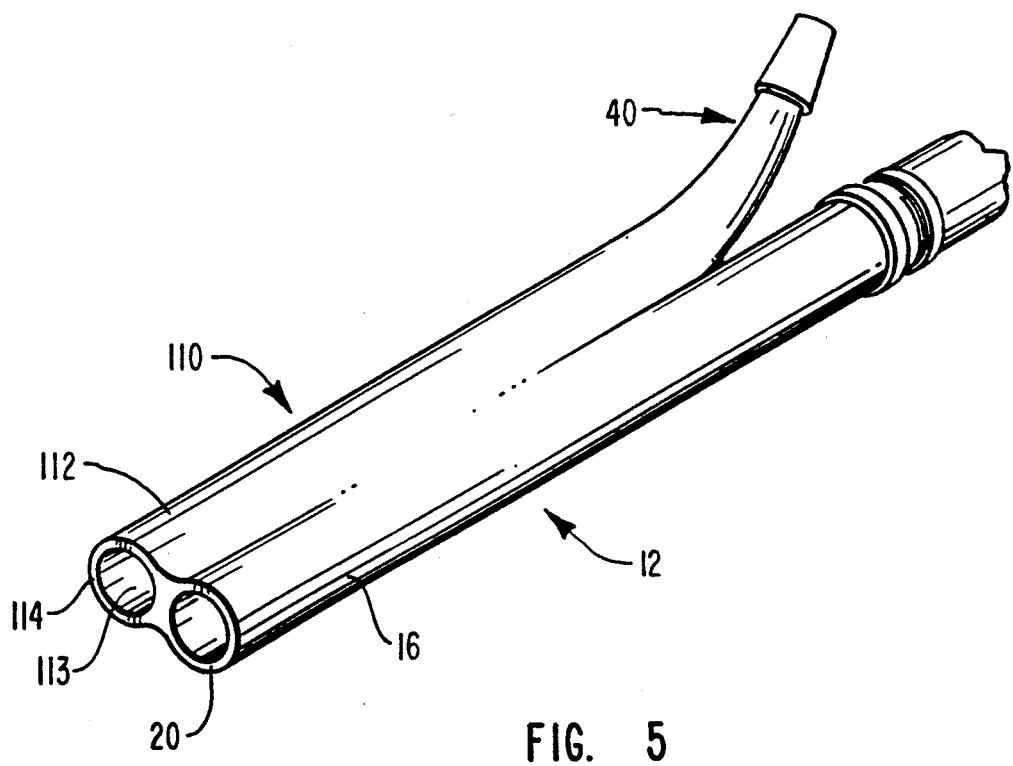
FIG. 5 is a perspective view of another embodiment of the invention showing a side-by-side arrangement of the probe and the smoke eliminator.

Smoke eliminator 14 also comprises a suction port 40 affixed to, or near, the proximal end 32 of tubular member 30, as shown. Suction port 40 is configured as an elongate tubular member 42, positioned so as to form an acute angle with tubular member 30, sloping away from tubular member 30 towards proximal end 32 thereof. In some embodiments suction port 40 is offset as shown in FIGS. 1 and 5.

An aperture 43 is fashioned in tubular member 30 so as to permit communication between the passageway of the suction port 40 and the annular space 36 between probe 12 and smoke eliminator 14. When a suction device (not shown) is coupled to suction port 40, smoke created at a target site by the action of a surgical agent thereto through surgical probe 12 is drawn from the vicinity of the target area into distal end 34 of tubular member 30. This movement of smoke thereby defines a fluid flow pathway for the inventive device.

Figure 4:
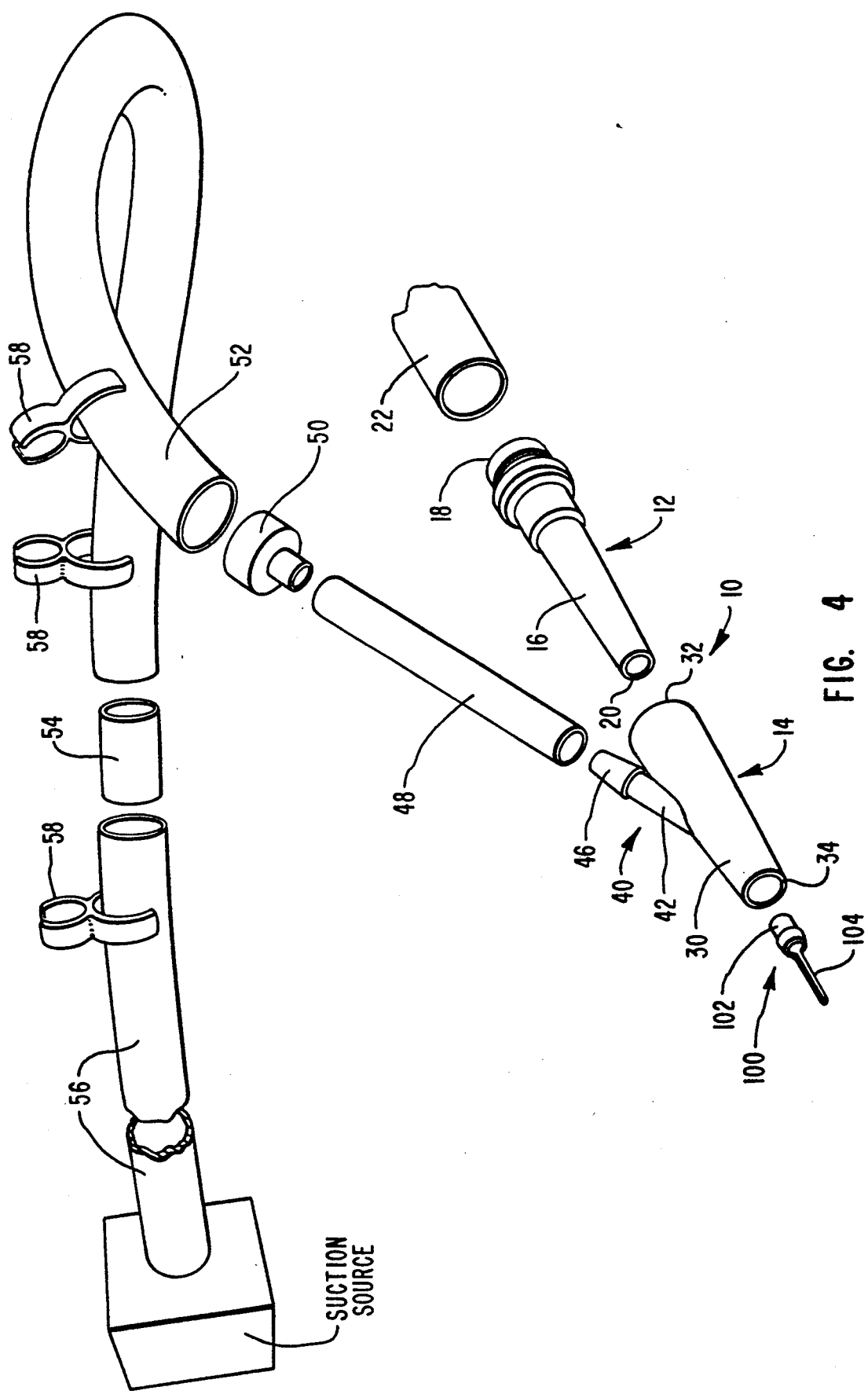
FIG. 4 is a partial exploded view showing the probe tip, the probe, the smoke eliminator, and the interconnecting tubing.

As shown best in FIG. 4, proximal end 46 of tubular member 42 is configured so as to engage by a slip fit a flexible tube 48 which serves to connect suction port 40 to a vacuum suction device (not shown). Flexible tube 48 is a relatively short hose having a smooth bore. A reducer 50 interconnects tube 48 to a longer and larger diameter smooth bore hose 52, which in turn is interconnected by a coupler 54 to another hose 56. Clips, such as 58, serve to attach hose 52 to an articulated arm or to the surgical agent source. Hose 56 is connected to a conventional vacuum suction device (not shown). Hoses 52 and 56 have a relatively large diameter and a smooth bore in order to minimize friction loss and also noise.

Tubular members 16 and 30 are preferably, tapered at distal ends 20 and 34 thereof, respectively, thereby as shown to afford a surgeon a clearer view of the target area.

Figure 6:
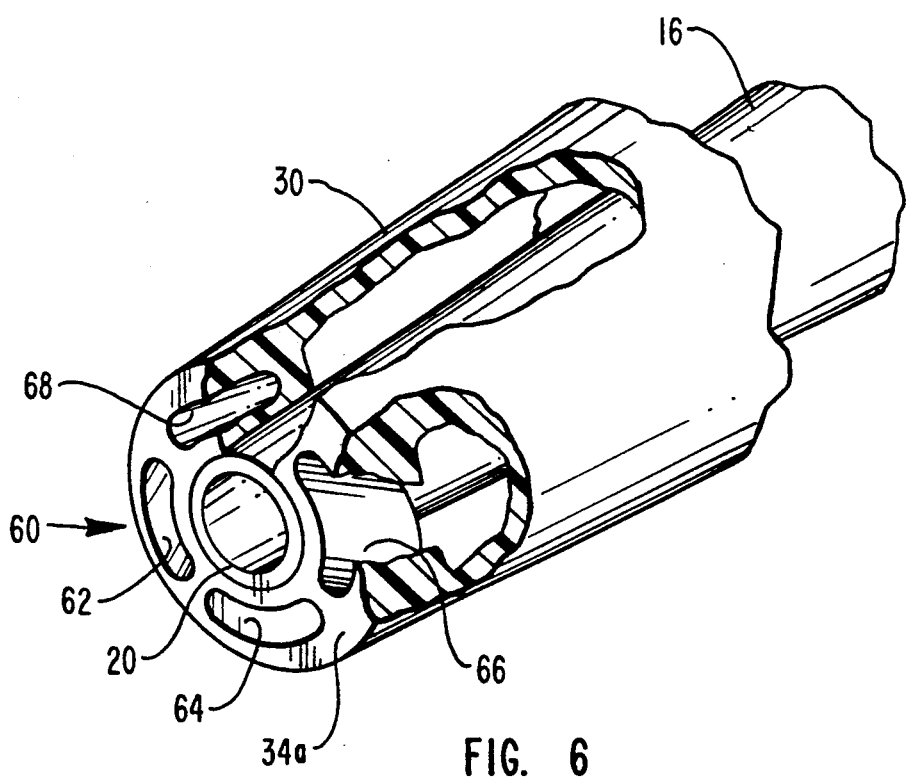
FIG. 6 is a cutaway section of the distal end of an inventive handpiece such as that shown in FIGS. 1-4 having a vortex-creating nozzle.

Smoke eliminator 14 also comprises, optionally, a nozzle 60, shown best in FIG. 6. Nozzle 60 is positioned at the distal end 342 of tubular member 30 and comprises a plurality, depicted as four in the figures, of nozzle orifices 62, 64, 66, 68, configured and positioned so as to create a vortex in their immediate vicinity upstream from distal end 34 of tubular member 30 in the fluid flow pathway defined above relative to the flow of smoke to tubular member 30 whenever vacuum port 40 is connected to a suction vacuum device. The nozzle orifices are angularly, as contrasted with longitudinally, configured, as shown, and serve to induce rotary motion in smoke in the space around the target area as the result of suction in annular space 36.

The invention also comprises, as an optional feature, a removable probe tip 100 as shown best in FIG. 4. The probe tip is configured so as to be removably attached to the distal end of handpiece 10 by attachment to either the distal end 34 of tubular member 30 or to the distal end 20 of tubular member 16. Probe tip 100 may be press fit, as depicted in FIG. 4, threadably engaged, or integrally molded with the handpiece 10.

As shown, the probe tip 100 comprises a short tubular member 102 having a segmental longitudinal extension 104 positioned on the perimeter of tubular member 102. The probe tip 100 is configured so as to approximately define the target area, and to automatically space the probe an appropriate predetermined distance from the target area. For instance, the probe tip 100 may be used to define the focal distance for a laser beam, while in other types of surgical procedures, such a probe tip it may not be appropriate. Thus, the probe tip 100 is fashioned so as to be removable.

The probe 12, the probe tip, and the smoke eliminator are preferably fashioned from plastic. A plastic such as polycarbonate is known to provide satisfactory results, although other plastics and even other materials may also be used.

By way of example, and not to be considered as limiting, the probe 12 may have length of approximately 3.6 inches and a diameter at proximal end 18 of approximately 0.7 inches tapering to 0.4 inches at distal end 20. The smoke eliminator may have a length of approximately 3 inches and a diameter of approximately 0.7 inches at proximal end 32 tapering to 0.5 inches at distal end 34. The replaceable probe tip 100 may have a tip length of approximately 1 inch.

Another embodiment of the invention is shown in FIG. 5. In this embodiment, the smoke eliminator 110 is configured so as to have an elongate tubular member 112 fixedly attached in a side-by-side fashion to the elongate tubular member 16 of the probe 12 by cementing or by encircling bands or cords. In this embodiment, the passageway 113 through tubular member 112 serves the same purpose as the annular space 36 in the previously described embodiment. In other respects, smoke eliminator 110 is similar to smoke eliminator 14 and like parts are given similar identifying numbers.

Figure 5A:
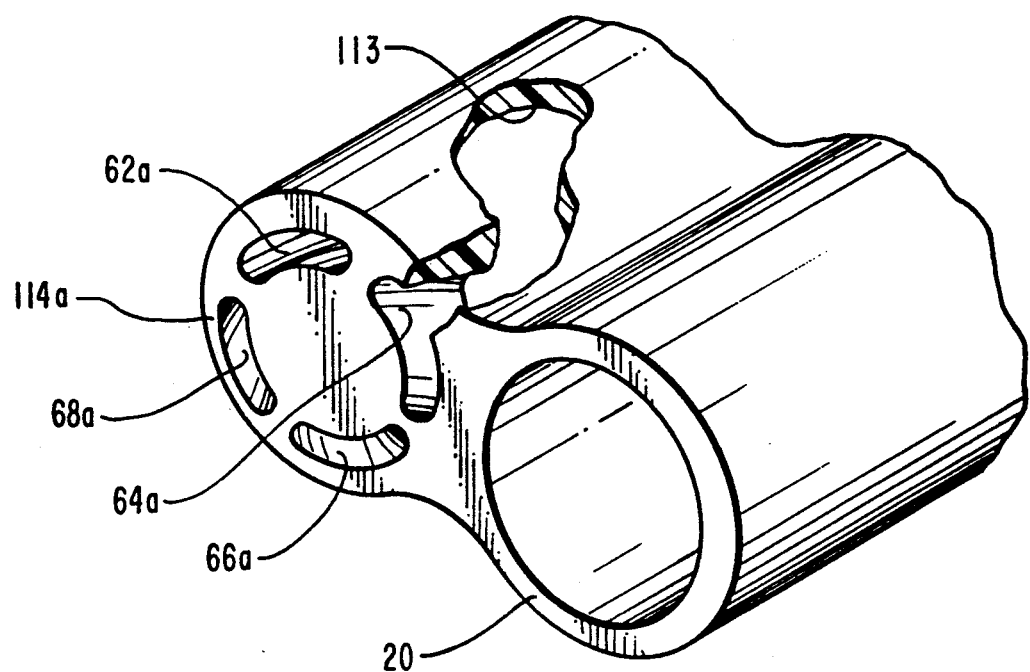
FIG. 5A is a cutaway section of the distal end of an inventive hand piece such as that shown in FIG. 5 having a vortex-creating nozzle.

Distal end 114 of elongate tubular member 112 may have a plurality of angularly directed nozzle orifices, such as described relative to FIG. 6 configured and positioned so as to create a vortex flow in the immediate vicinity when tubular member 112 is connected to a suction device. Toward this end tubular member 112 will communicate with a suction port 40, which may or may not be offset therefrom. FIG. 5A depicts such a set of angularly directed nozzles 62a, 64a, 66a, and 68a at distal end 114a of tubular member 112.

Figure 7:
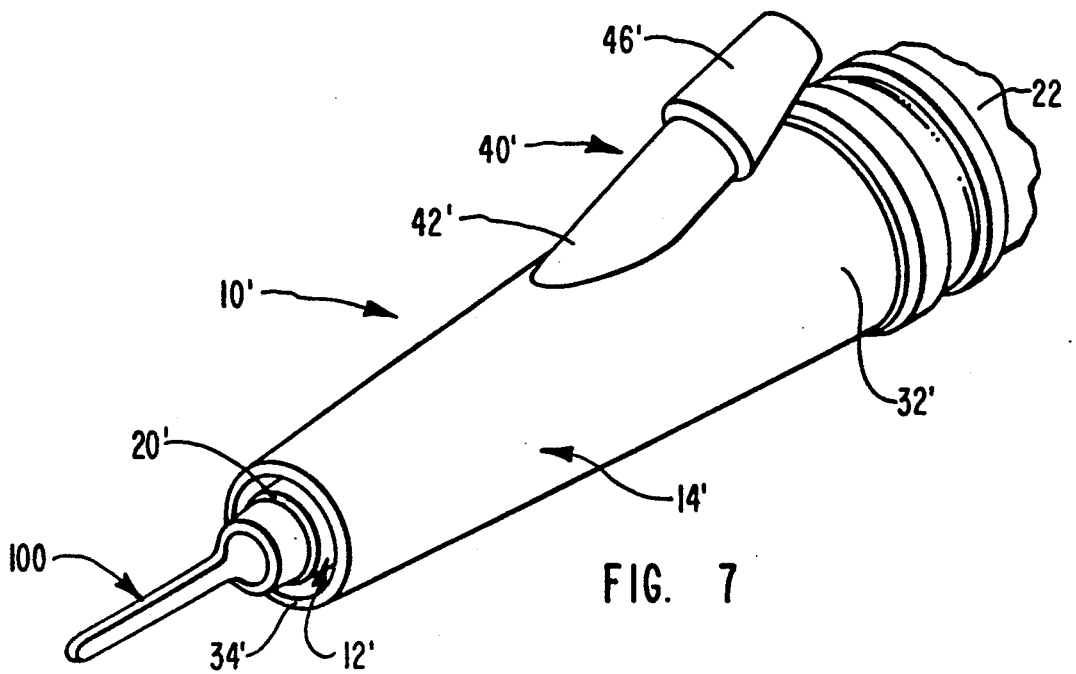
FIG. 7 is a perspective view of another embodiment of the invention having a non-offset vacuum port.
Figure 8:
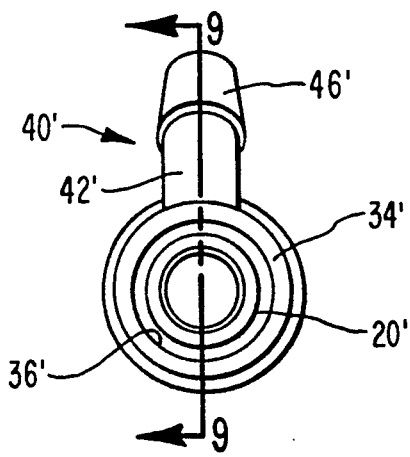
FIG. 8 is an end elevation view of the handpiece of FIG. 7.
Figure 9:
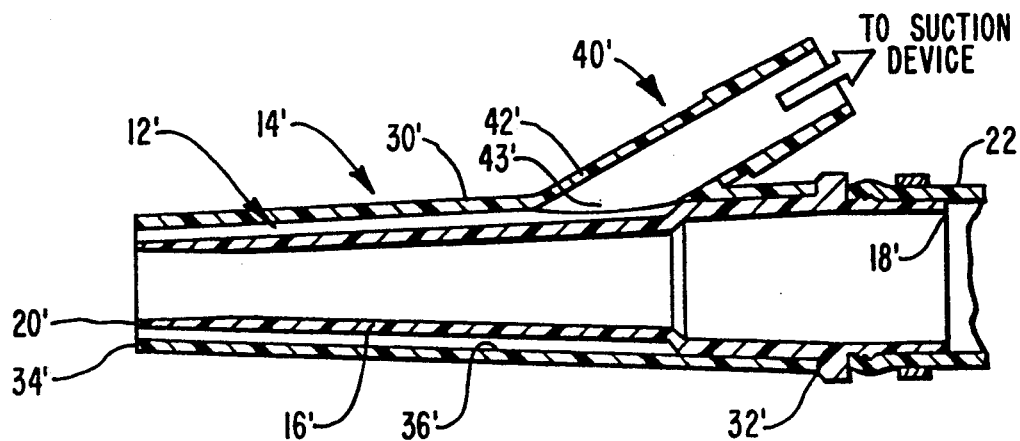
FIG. 9 is a cross-sectional view taken along lines 9—9 of FIG. 8.

Another embodiment of the invention is shown in FIGS. 7, 8, and 9. This embodiment is similar to that shown in FIGS. 1, 4 except that the vacuum suction port 40' is not offset from the axis of smoke eliminator 14'. Parts in FIGS. 7-9 similar to parts in FIGS. 1-4 are numbered similarly to those of FIGS. 1, and 4 except that the numbers in FIGS. 7-9 are primed. The present invention may be embodied in other specific forms and for other specific uses without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A surgical handpiece for use in applying to a target area on or in the body of a patient a surgical agent that creates an unwanted smoke plume in the vicinity of the target area, the handpiece in combination with a suction device located external to the body of the patient removing the smoke plume from the vicinity of the target area, the handpiece comprising:

(a) a surgical probe comprising a first conduit, said first conduit having a proximal end coupleable to a source of the surgical agent and a distal end opposite therefrom, said surgical probe being configured so as to apply the surgical agent to the target area by orienting the distal end of the first conduit theretoward; and (b) a smoke eliminator comprising:

(i) a second conduit affixed to the first conduit, said second conduit having a distal end, a proximal end, and an elongate axis, the distal end of the second conduit being disposed in proximal relation to the distal end of the first conduit to define thereat a distal end of said handpiece (ii) means for coupling the second conduit to the suction device, thereby to apply suction to the vicinity of the target area and to draw the smoke plume from the vicinity of the target area into the distal end of the second conduit and through the second conduit, defining thereby a fluid flow pathway for the smoke plume; and (iii) means for creating a vortex in the smoke plume upstream in said fluid flow pathway from the distal end of the second conduit when the second conduit is coupled to the suction device.

2. A surgical handpiece as defined in claim 1, wherein the means for creating a vortex comprises a plurality of angularly directed nozzle orifices positioned peripherally around the distal end of the second conduit.

3. A surgical handpiece as defined in claim 1, wherein the means for coupling comprises an elongate vacuum port communicating with the second conduit, said vacuum port having an elongate axis disposed in an offset relationship to the elongate axis of the second conduit.

4. A surgical handpiece as defined in claim 1, wherein the first conduit and the second conduit are concentric with respect to each other and define therebetween an annular space open at the distal end thereof.

5. A surgical handpiece as defined in claim 1 wherein the first conduit and the second conduit are positioned in a side-by-side relationship with respect to each other.

6. A surgical handpiece as defined in claim 1, wherein the surgical agent comprises a surgical laser beam.

7. A surgical handpiece as defined in claim 6, further comprising a removable elongate probe tip to assist in locating a focal point of the surgical laser beam, the probe tip comprising:
   (a) a proximal end which cooperatively engages the distal end of the handpiece, and
   (b) a narrow elongate targeting member extending approximately the same distance from the proximal end of the probe tip as the distance of the focal point of the surgical laser beam from the distal end of the handpiece.

8. A surgical handpiece for use in applying a surgical laser beam to a target area of the body of a patient, the handpiece in combination with a suction device located external to the body of the patient removing from the vicinity of the target area the smoke and vaporized particles created by the laser beam, the handpiece comprising:
   (a) a surgical probe comprising a first elongate tubular member having a distal end and a proximal end, wherein the proximal end is adapted for attachment to a source of the laser beam, and the distal end is open to permit passage of a laser beam therethrough; and
   (b) a smoke eliminator comprising:
      (i) a second elongate tubular member having an open distal end, a proximal end opposite therefrom, and an elongate axis, said second tubular member being affixed to the first tubular member with the distal end of the second tubular member being disposed in proximal relation to the distal end of the first tubular member to define thereat a distal end of said handpiece,
      (ii) a vacuum port affixed to the proximal end of the second tubular member and communicating therewith, said vacuum port being configured to enable selective coupling of the smoke eliminator to the suction device, thereby to apply suction to the vicinity of the target area and to draw the smoke and vaporized particles from the vicinity of the target area of the second tubular member through the distal end thereof, defining thereby a fluid flow pathway for the smoke and vaporized particles; and
      (iii) means for creating a vortex in the smoke and vaporized particles upstream in said fluid flow pathway from the distal end of the second tubular member.

9. A surgical handpiece as defined in claim 8, wherein the first tubular member and the second tubular member are concentric with respect to each other and define therebetween an annular space, said annular space opening at the distal ends of the first and second tubular members.

10. A surgical handpiece as defined in claim 9, wherein the means for creating a vortex comprises a plurality of angularly directed nozzle orifices positioned within the annular space at the distal end of the first and second tubular members.

11. A surgical handpiece as defined in claim 9, wherein the vacuum port comprises a third elongate tubular member having a distal end, a proximal end and an elongate axis, the third tubular member being fixedly attached in an offset fashion at the distal end thereof to the proximal end of the second elongate tubular member, the elongate axis of the third tubular member in a first planar projection being substantially parallel to and offset from the elongate axis of the second elongate tubular member, and in a second planar projection which is orthogonal to the first planar projection the elongate axis of the third tubular member forming an acute angle with the elongate axis of said second elongate tubular member; the third tubular member being configured so as to form a passageway communicating with the annular space between the first and second tubular members; and the vacuum port further comprising means at the proximal end of the third tubular member for separably connecting to the third tubular member a conduit communicating with the suction device.

12. A surgical handpiece as defined in claim 11, further comprising a plurality of angularly directed nozzle orifices positioned within the annular space at point distal end of said handpiece.

13. A surgical handpiece as defined in claim 8, further comprising a removable elongate probe tip to assist in locating a focal point of the surgical laser beam, the probe tip comprising:
   (a) a proximal end which cooperatively engages the distal end of the handpiece, and
   (b) a narrow elongate targeting member extending approximately the same distance from the proximal end of the probe tip as the distance of the focal point of the surgical laser beam from the distal end of the handpiece.

14. A surgical handpiece as defined in claim 13, wherein the proximal end of the probe tip is press fitted to the distal end of the first tubular member.

15. A surgical handpiece as defined in claim 13 wherein the proximal end of the probe tip and the distal end of the first tubular member are threaded so as to provide threaded engagement therebetween.

16. A surgical handpiece as defined in claim 8 wherein the second tubular member is adjacent to, and is affixed to, the first tubular member in a side-by-side fashion.

17. A surgical handpiece as defined in claim 16, wherein the means for creating a vortex comprises a plurality of angularly directed nozzle orifices positioned in the distal end of the second tubular member.

18. A surgical handpiece as defined in claim 16, wherein the vacuum port comprises a third elongate tubular member having a distal end, a proximal end, and an elongate axis, the third tubular member being fixedly attached in an offset fashion at the distal end thereof to the proximal end of the second elongate tubular member, the elongate axis of the third tubular member in a first planar projection being substantially parallel to and offset from the elongate axis of the second elongate tubular member, and in a second planar projection which is orthogonal to the first planar projection with the elongate axis of the third tubular member forming an acute angle with the elongate axis of said second elongate tubular member; the third tubular member being configured so as to form a passageway communicating with said second tubular member; and the vacuum port further comprising means at the proximal end of the third tubular member for separably connecting to the third tubular member a conduit communicating with the suction device.

19. A surgical handpiece as defined in claim 18, further comprising a plurality of angularly directed nozzle orifices positioned in the distal end of the second tubular member.

20. A surgical handpiece as defined in claim 8, wherein the first tubular member and the second tubular member are affixed at the proximal ends thereof.

21. A surgical handpiece as defined in claim 20, wherein the first tubular member and the second tubular member are comprised of plastic.

* * * * *

UNITED STATES PATENT AND TRADEMARK OFFICE
CERTIFICATE OF CORRECTION

PATENT NO. : 5,181,916

DATED : January 26, 1993

INVENTOR(S) : VALDON G. REYNOLDS et al.

It is certified that error appears in the above-identified patent and that said Letters Patent is hereby corrected as shown below:

```
Column 2, line 27, "nozzles" should be --nozzle--
Column 3, line 42, "except" should be --with--
Column 4, line 16, delete "likewise not"
Column 5, line 3, "distal end 342" should be --distal end 34a--
Column 5, line 34, after "smoke eliminator" insert --14--
Column 5, line 34, after "probe tip" insert --100--
Column 8, line 12, "point" should be --said--
```

Signed and Sealed this

Twenty-first Day of June, 1994

Attest:

BRUCE LEHMAN

Attesting Officer

Commissioner of Patents and Trademarks